US00PP11980P2

(12) United States Plant Patent
Cunneen

(10) Patent No.: US PP11,980 P2
(45) Date of Patent: Jul. 10, 2001

(54) ARGYRANTHEMUM PLANT NAMED 'SUGAR BUTTON'

(75) Inventor: Thomas Michael Cunneen, Theresa Park (AU)

(73) Assignee: University of Sydney Plant Breeding Institute, Cobbitty (AU)

( * ) Notice: Subject to any disclaimer, the term of this patent is extended or adjusted under 35 U.S.C. 154(b) by 0 days.

(21) Appl. No.: 09/257,092

(22) Filed: Feb. 22, 1999

(51) Int. Cl.[7] ..... A01H 5/00
(52) U.S. Cl. ..... Plt./263
(58) Field of Search ..... Plt./263

(56) References Cited

U.S. PATENT DOCUMENTS

P.P. 11,040 * 8/1999 Cunneen ..... Plt./263

OTHER PUBLICATIONS

UPOV–ROM GTITM Computer Database 2000/02 GTI JOUVE Retrieval Software, citations for 'Sugar Button', 2000.*

'Sugar Button' Application No: 96/186 Plant Varieties Journal, vol. 10 (3): p. 28, 1997.*

* cited by examiner

*Primary Examiner*—Bruce R. Campell
*Assistant Examiner*—Wendy A Baker
(74) *Attorney, Agent, or Firm*—C. A. Whealy

(57) ABSTRACT

A distinct cultivar of Marguerite Daisy plant named Sugar Button, characterized by its upright, mounding and compact plant habit; green-colored stems; freely branching, dense plants with short internodes; freely flowering with numerous inflorescences per plant; medium-sized anemone-type inflorescences; and pure white ray and bright yellow disc florets that gradually become white with development.

1 Drawing Sheet

BACKGROUND OF THE INVENTION

The present invention relates to a new and distinct cultivar of Marguerite Daisy plant, botanically known as *Argyranthemum frutescens* and referred to by the cultivar name Sugar Button.

The new cultivar is a product of a planned breeding program conducted by the Inventor in Cobbitty, New South Wales, Australia. The objective of the breeding program was to develop compact and freely-flowering Marguerite daisies that have inflorescences with good form and floret color.

The new cultivar originated from a cross made by the Inventor in 1993 of a proprietary selection of *Argyranthemum frutescens* identified as number AB5003, as the male or pollen parent, with a proprietary selection of *Argyranthemum frutescens* identified as number AB50052, as the female or seed parent. The cultivar Sugar Button was discovered and selected by the Inventor as a flowering plant within the progeny of the stated cross in a controlled environment in Cobbitty, New South Wales, Australia.

Plants of the new Marguerite Daisy are different from plants of the male parent, the selection number AB5003, in plant height, plant diameter, leaf color, inflorescence size and ray floret color.

Plants of the new Marguerite Daisy are different from plants of the female parent, the selection number AB50052, in plant diameter, inflorescence size and ray floret color.

Asexual reproduction of the new cultivar by terminal cuttings and by tissue culture in Cobbitty, New South Wales, Australia, has shown that the unique features of this new Marguerite Daisy are stable and are reproduced true to type in successive propagations.

SUMMARY OF THE INVENTION

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Sugar Button' which distinguish 'Sugar Button' as a new and distinct cultivar:

1. Upright, mounding and compact plant habit.
2. Green-colored stems, no anthocyanin.
3. Freely branching, dense plants with short internodes.
4. Freely flowering with numerous inflorescences per plant.
5. Medium-sized anemone-type inflorescences.
6. Pure white ray and bright yellow disc florets that gradually become white with development.

Plants of the new Marguerite Daisy can be compared to plants of the cultivar Sugar and Ice, disclosed in U.S. Plant Pat. No. 11,040. In side-by-side comparisons conducted in Cobbitty, New South Wales, Australia, plants of the new Marguerite Daisy are slightly taller and more narrow than plants of the cultivar Sugar and Ice. In addition, plants of the new Marguerite Daisy have shorter leaves and smaller inflorescences than plants of Sugar and Ice.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of four typical plants of 'Sugar Button' in a 25-cm container.

The photograph at the bottom of the sheet comprises close-up views of developing inflorescences (top) and upper and lower leaf surfaces (bottom). Floret and foliage colors in the photographs may appear different from the actual colors due to light reflectance.

DETAILED BOTANICAL DESCRIPTION

The following observations, measurements and values describe a 25-cm container of four plants of the new Marguerite Daisy grown in Bonsall, Calif., in full sun with day temperatures ranging from 18 to 35° C. and night temperatures ranging from 13 to 18° C.

Color references are made to The Royal Horticultural Society Colour Chart except where general terms of ordinary dictionary significance are used.

Botanical classification: *Argyranthemum frutescens* cultivar Sugar Button.

Parentage:

*Male or pollen parent.*—Proprietary selection of *Argyranthemum frutescens*, identified as number AB5003.

*Female or seed parent.*—Proprietary selection of *Argyranthemum frutescens* identified as number AB50052.

Propagation:

*Type.*—Terminal cuttings.

*Time to initiate roots.*—Summer: About 10 days at a temperatures of 25° C. Winter: About 15 days at a temperatures of 20° C.

*Time to develop roots.*—Summer: About 15 days at a temperatures of 25° C. Winter: About 20 days at a temperatures of 20° C.

*Rooting description.*—Numerous, fibrous to thick, and freely branching.

Plant description:

*General appearance.*—Inverted triangle; upright, mounding and compact plant habit. Short internodes result in an upright, but very compact plant habit. Pinnatifid foliage and erect flower stems that hold the inflorescences above the foliage. Appropriate for various sizes and types of containers.

*Crop time.*—About 8 to 12 weeks are required to produces a finished flowering plant in a 10-cm container from a rooted cutting.

*Plant height.*—About 32 cm from soil level to top of inflorescences.

*Plant width.*—About 22 cm.

*Branching.*—Freely basal branching, about five lateral per plant; removal of the terminal apex (pinching) is usually not required.

*Vigor.*—Moderately vigorous.

*Lateral branches.*—Length: About 30 cm. Diameter: About 4 mm. Internode length: About 5 to 10 mm. Texture: Glabrous; woody at base.

*Stem color.*—Green, 144B, no anthocyanin.

*Foliage description.*—Arrangement: Alternate, single. Quantity of leaves per lateral branch: About 25. Shape: Pinnatifid. Apex: Three-parted. Base: Attenuate; clasping; sessile. Margin: Five to seven-lobed; deeply incised. Length: About 6.5 cm. Width: About 3.5 to 4 cm. Texture: Glabrous and smooth. Durability to stresses: Good, very durable. Leaves have a waxy cuticle that resists water loss. Color: Young leaves, upper surface: 138A. Young leaves, lower surface: More yellow than 138A. Mature leaves, upper surface: 137A. Mature leaves, lower surface: More yellow than 137B. Venation, upper surface: 137A. Venation, lower surface: 137B.

Flowering description:

*Flowering habit.*—Inflorescences on long peduncles held above the foliage. Anemone-type composite inflorescence form. Inflorescences form at upper leaf axils. Florets arranged acropetally on a capitulum. Inflorescences last about one week. Inflorescences persistent.

*Quantity of inflorescences.*—Freely flowering; typically about 6 or 7 inflorescences and buds per lateral stem; usually about 30 to 35 inflorescences and buds per plant.

*Natural flowering season.*—Natural flowering season is spring to early fall. Plants flower continuously during this period.

*Inflorescence size.*—Diameter: About 4 cm. Depth (height): About 1.2 cm. Disc diameter: About 2 cm.

*Fragrance.*—None.

*Ray florets.*—Aspect: Initially flat; outer ray florets reflex downward as inflorescences develop. Quanitity per inflorescence and arrangement: About 24 ray florets arranged in a double whorl. Shape: Ligulate. Apex: Rounded. Base: Attenuate. Margin: Entire. Length: About 1.5 cm. Width: About 5 mm. Texture: Smooth, velvety. Color: When opening and fully opened, upper surface: 155B to 155C. When opening and fully opened, lower surface: 155C.

*Disc florets.*—Shape: Tubular, salverform; 5-lobed, flared at apex; outer florets split on outer surface resulting in a fringed appearance. Quantity per inflorescence: Numerous, usually about 208. Disc floret length: About 8 to 10 mm. Disc floret width: About 3 mm. Color: Initially bright yellow becoming white with development. Immature: 5A to 9A. Mature: Outer (oldest) florets: 155A. Inner (youngest) florets: 155A at base; lobes gold-tipped, 5A to 9A.

*Phyllaries.*—Quantity per inflorescence and arrangement: About 26 per inflorescence; imbricate, several rows, tightly pressed to the receptacle. Aspect: Cupped. Shape: Elliptic. Apex: Broadly acute. Margin: Entire, outer edges slightly membranous. Length: About 1.4 cm. Color: Upper surface: 144A. Lower surface: 146A.

*Peduncle.*—Length, first peduncle: About 7 to 9 cm. Length, fourth peduncle: About 5 cm. Strength: Moderately strong, inflorescences held above foliage. Angle: Acute. Texture: Smooth. Color: 144A.

*Inflorescence bud.*—Shape: Spherical to cupped. Length: About 1.2 cm. Diameter: About 8 mm. Color: 157A.

*Reproductive structures.*—Androecium: Stamens: About five, very tiny rudimentary stamens in central disc florets only; functionally sterile. Anther color: 5A. Pollen: Scarce. Pollen color: 5A. Gynoecium: Present on ray florets only. Pistil number: One per floret. Pistil length: About 2 mm. Style length: About 1 mm. Style color: 144C. Stigma shape: Bilobed. Stigma color: 4A. Ovary color: 144C.

Disease resistance: Resistance to pathogens common to Argyranthemum has not been observed.

Seed production: Seed production is typically not observed.

It is claimed:

1. A new and distinct Marguerite Daisy plant named 'Sugar Button', as illustrated and described.

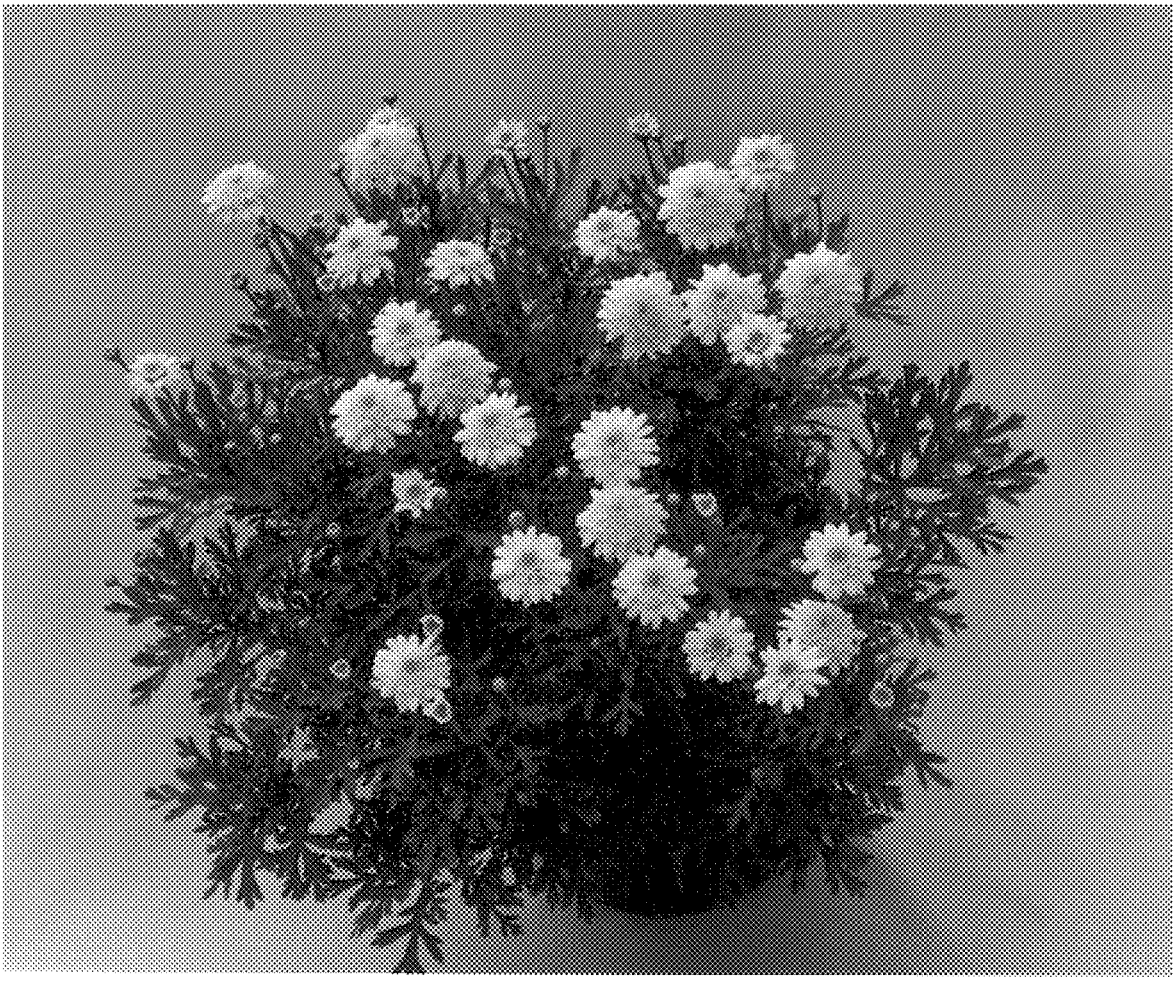
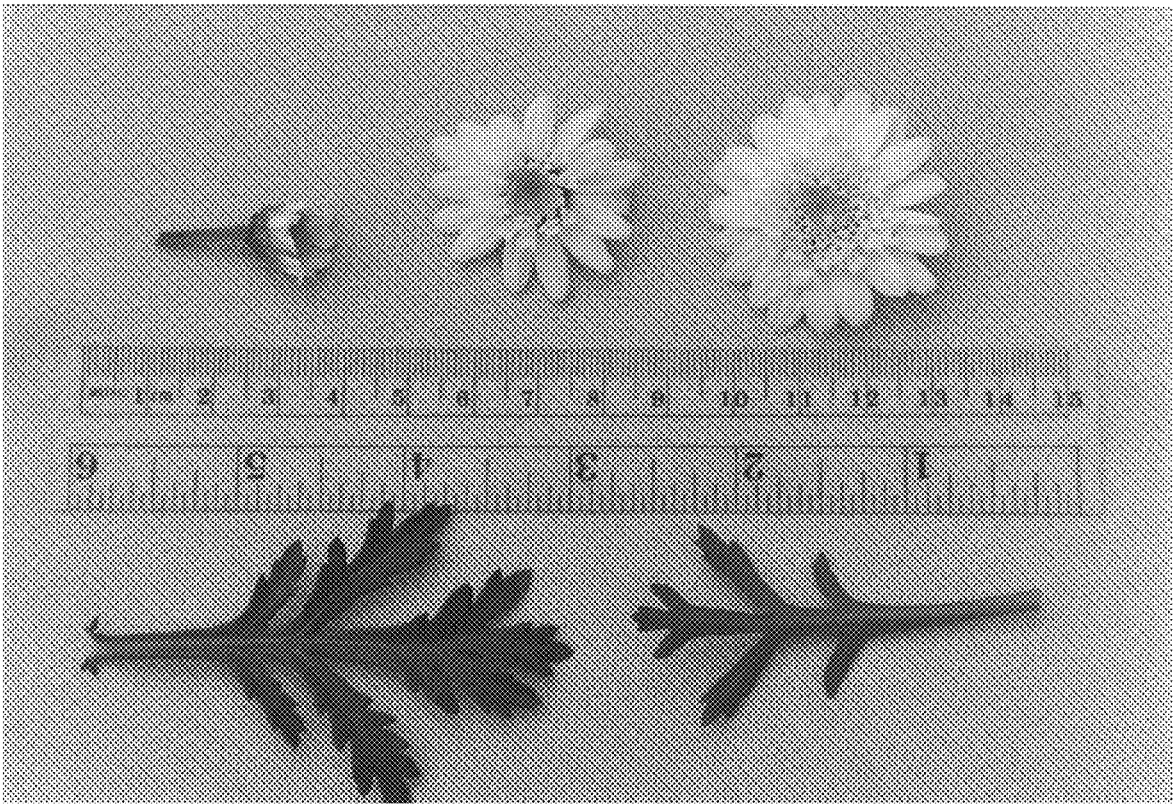

* * * * *